(12) United States Patent
Nguyen Thi Tai et al.

(10) Patent No.: US 12,708,570 B2
(45) Date of Patent: Aug. 18, 2026

(54) ABSORBENT BODY FOR USE IN AN ABSORBENT ARTICLE

(71) Applicant: Kimberly-Clark Worldwide, Inc., Neenah, WI (US)

(72) Inventors: Linh Nguyen Thi Tai, Ho Chi Minh (VN); Minjae Lee, Ho Chi Minh (VN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 297 days.

(21) Appl. No.: 18/576,188

(22) PCT Filed: Apr. 25, 2022

(86) PCT No.: PCT/US2022/026123
§ 371 (c)(1),
(2) Date: Jan. 3, 2024

(87) PCT Pub. No.: WO2023/009191
PCT Pub. Date: Feb. 2, 2023

(65) Prior Publication Data

US 2024/0382352 A1 Nov. 21, 2024

(30) Foreign Application Priority Data

Jul. 29, 2021 (VN) .............................. 1-2021-04704

(51) Int. Cl.
*A61F 13/536* (2006.01)
*A61F 13/49* (2006.01)
(Continued)

(52) U.S. Cl.
CPC .......... *A61F 13/536* (2013.01); *A61F 13/515* (2013.01); *A61F 13/49* (2013.01); *A61F 2013/530481* (2013.01); *A61F 13/537* (2013.01)

(58) Field of Classification Search
CPC .... A61F 13/536; A61F 13/515; A61F 13/537; A61F 13/49; A61F 2013/530481
See application file for complete search history.

(56) References Cited

U.S. PATENT DOCUMENTS 5,423,787 A 6/1995 Nellberg
5,941,863 A * 8/1999 Guidotti ................ A61F 13/535 604/374

(Continued)

FOREIGN PATENT DOCUMENTS

EP 0617601 B2 7/2002
JP 2009000351 A * 1/2009 ......... A61F 13/4756

(Continued)

OTHER PUBLICATIONS

Ajmeri, J.R. et al., "Developments in the use of nonwovens for disposable hygiene products", Advances in Technical Nonwovens, 2016, https://sci-hub.se/https://doi.org/10.1016/B978-0-08-100575-0.00018-8.

*Primary Examiner* — Guy K Townsend
(74) *Attorney, Agent, or Firm* — KIMBERLY-CLARK WORLDWIDE, INC.

(57) ABSTRACT

An absorbent body for use in an absorbent article can have an improved body exudate distribution capability. The absorbent body can have an anterior region, a posterior region, and a crotch region located between the anterior region and the posterior region. An exudate capture zone can be located within the crotch region of the absorbent body. The exudate capture zone can have a primary compressed element which has a longitudinal direction length greater than a transverse direction width. The primary compressed element within the exudate capture zone can be encircled by a plurality of primary compressed points. Each of the encircled primary compressed element and the encircling primary compressed points can provide an initial pathway (Continued)

for body exudates to travel from the body facing surface of the absorbent body and into other regions of the absorbent body in both the longitudinal direction and transverse direction of the absorbent body.

20 Claims, 10 Drawing Sheets

(51) Int. Cl.
*A61F 13/515* (2006.01)
*A61F 13/537* (2006.01)
*A61F 13/53* (2006.01)

(56) References Cited

U.S. PATENT DOCUMENTS 5,986,167 A * 11/1999 Arteman .......... A61F 13/53747 604/383
6,458,111 B1 * 10/2002 Onishi .......... A61F 13/495 604/385.01
6,551,295 B1 * 4/2003 Schmidt .......... A61F 13/5376 604/385.01
6,570,057 B1 * 5/2003 Schmidt .......... A61F 13/534 604/378
6,664,439 B1 * 12/2003 Arndt .......... A61F 13/15203 604/374
6,720,471 B1 * 4/2004 Arndt .......... A61F 13/53747 604/378
6,869,423 B2 * 3/2005 Onishi .......... A61F 13/495 604/385.01
7,189,448 B2 3/2007 Raidel et al.
7,378,567 B2 * 5/2008 Mangold .......... A61F 13/539 156/196
7,727,212 B2 * 6/2010 Sakai .......... A61F 13/539 604/383
7,772,455 B1 * 8/2010 Roe .......... A61F 13/51113 604/385.01
7,838,723 B1 * 11/2010 Schmidt .......... A61F 13/15203 604/385.01
8,556,875 B2 * 10/2013 Takahashi .......... A61F 13/535 604/385.101
8,927,803 B2 * 1/2015 Sakai .......... A61F 13/4756 604/385.101
10,052,242 B2 * 8/2018 Bianchi .......... A61F 13/535
10,285,873 B2 * 5/2019 Barbosa .......... A61F 13/533
10,675,188 B2 * 6/2020 Ludwig .......... A61F 13/49017
11,344,454 B2 * 5/2022 Ludwig .......... A61F 13/15203
11,399,992 B2 * 8/2022 Tally .......... A61F 13/4906
11,452,646 B2 * 9/2022 Tally .......... A61F 13/4758
2002/0111594 A1 * 8/2002 Onishi .......... A61F 13/495 604/385.28
2003/0045851 A1 * 3/2003 Vartiainen .......... A61F 13/535 604/383
2006/0184151 A1 * 8/2006 Onishi .......... A61F 13/15203 604/385.24
2006/0287636 A1 * 12/2006 Sakai .......... A61F 13/532 604/385.101
2008/0103287 A1 * 5/2008 Chino .......... C08C 19/22 528/421
2011/0208147 A1 * 8/2011 Kawakami .......... A61F 13/5323 604/385.01
2012/0078209 A1 * 3/2012 Sakai .......... A61F 13/53 604/378
2012/0323195 A1 * 12/2012 Ehrnsperger .......... A61F 13/53 604/366
2013/0079740 A1 * 3/2013 Ehrnsperger .......... A61L 15/58 604/367
2013/0331806 A1 * 12/2013 Rosati .......... A61F 13/53743 604/366
2014/0005622 A1 * 1/2014 Wirtz .......... A61F 13/539 604/366
2014/0005623 A1 * 1/2014 Wirtz .......... A61F 13/53418 604/366
2014/0121487 A1 * 5/2014 Faybishenko .......... G16H 40/63 600/365
2014/0249497 A1 * 9/2014 Bissah .......... A61F 13/53 604/374
2015/0065981 A1 * 3/2015 Roe .......... A61F 13/4756 604/378
2015/0157251 A1 * 6/2015 Nelson .......... A61F 13/15739 600/580
2015/0282998 A1 * 10/2015 Arizti .......... A61F 13/51104 604/385.19
2015/0313769 A1 * 11/2015 Dahl .......... A61F 13/15756 604/365
2016/0089277 A1 * 3/2016 Barbosa .......... A61F 13/51108 604/378
2017/0246052 A1 * 8/2017 Ludwig .......... A61F 13/15585
2017/0246056 A1 * 8/2017 Tagomori .......... A61F 13/47272
2017/0252015 A1 * 9/2017 Barnhorst .......... A61F 13/51405
2018/0049929 A1 * 2/2018 Konawa .......... A61F 13/535
2018/0369029 A1 * 12/2018 Barnhorst .......... A61F 13/535
2020/0337914 A1 * 10/2020 Onishi .......... A61F 13/532

FOREIGN PATENT DOCUMENTS

JP 6073619 B2 2/2017
JP 2021074070 A * 5/2021
WO 1997018783 A1 5/1997

* cited by examiner

ABSORBENT BODY FOR USE IN AN ABSORBENT ARTICLE

BACKGROUND

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

One problem with such conventional absorbent articles is that the body exudates are usually not well absorbed by the absorbent article. The body exudates may remain on and/or within an upper layer of the absorbent article rather than moving towards a lower layer of the absorbent article. Body exudates remaining on and/or within an upper layer of the absorbent article can result in a feeling of wetness and discomfort for the wearer of the absorbent article. This can ultimately lead to a wearer of the absorbent article having a feeling of early failure of the absorbent article as the body exudates to be absorbed cannot be efficiently spread throughout the absorbent article. If the body exudates to be absorbed cannot be efficiently spread through the absorbent article, they may run off the edge of the absorbent article causing leakage and staining.

As a result, there remains a need for an improved absorbent body for use in an absorbent article that has an improved body exudate distribution capability.

SUMMARY

In various embodiments, an absorbent body can have a longitudinal direction and a transverse direction; a longitudinal direction axis and a transverse direction axis; an anterior region, a posterior region, and a crotch region located between the anterior region and the posterior region; an exudate capture zone located within the crotch region, the exudate capture zone can have a first primary compressed element having a first longitudinal direction axis, a first longitudinal direction length, and a first transverse direction width, wherein the first longitudinal direction length is greater than the first transverse direction width and wherein the first longitudinal direction axis is parallel with the longitudinal direction axis of the absorbent body; a plurality of primary compressed points encircling the first primary compressed element wherein each of the plurality of primary compressed points has a second longitudinal direction length and a second transverse direction width, wherein the first longitudinal direction length of the first primary compressed element is greater than the second longitudinal direction length and the second transverse direction width of each of the primary compressed points of the plurality of primary compressed points encircling the first primary compressed element.

In various embodiments, the first longitudinal direction length of the first primary compressed element is from 7 to 20 mm and the first transverse direction width of the first primary compressed element is from 1 to 4 mm. In various embodiments, the second longitudinal direction length of each of the primary compressed points of the plurality of primary compressed points is from 1 to 4 mm and wherein the second transverse direction width of each of the primary compressed points of the plurality of primary compressed points is from 1 to 4 mm.

In various embodiments, the first longitudinal direction axis of the first primary compressed element is aligned in the longitudinal direction with a second longitudinal direction axis of one of the primary compressed points of the plurality of primary compressed points. In various embodiments, the aligned primary compressed element and primary compressed point are separated from each other by a first distance, in the longitudinal direction of the absorbent body, from 2 to 10 mm.

In various embodiments, the absorbent body can further have a second primary compressed element parallel with the first primary compressed element and encircled by the plurality of primary compressed points, wherein the second primary compressed element has a second longitudinal direction axis, a second longitudinal direction length, and a second transverse direction width, wherein the second longitudinal direction length is greater than the second transverse direction width and wherein the second longitudinal direction axis is parallel with the longitudinal direction axis of the absorbent body. In various embodiments, the second longitudinal direction length of the second primary compressed element is from 7 to 20 mm and the second transverse direction width of the second primary compressed element is from 1 to 4 mm.

In various embodiments, the absorbent body can further have a plurality of secondary compressed elements within the crotch region. In various embodiments, one of the plurality of secondary compressed elements has a second longitudinal direction axis which is aligned in the longitudinal direction with the first longitudinal direction axis of the first primary compressed element and wherein the first primary compressed element is separated, in the longitudinal direction, from the aligned secondary compressed element by a distance of less than 10 mm.

In various embodiments, the absorbent body can further have a plurality of secondary compressed points within the crotch region. In various embodiments, the absorbent body can further have a plurality of tertiary compressed elements in each of the anterior region and posterior region of the absorbent body. In various embodiments, the absorbent body can further have a plurality of tertiary compressed points in each of the anterior region and posterior region of the absorbent body.

In various embodiments, the proportion of the area of the compressed element and compressed points with respect to the area of the absorbent body is less than 15%.

In various embodiments, the absorbent body can be incorporated into an absorbent article.

DETAILED DESCRIPTION

Figure 1:
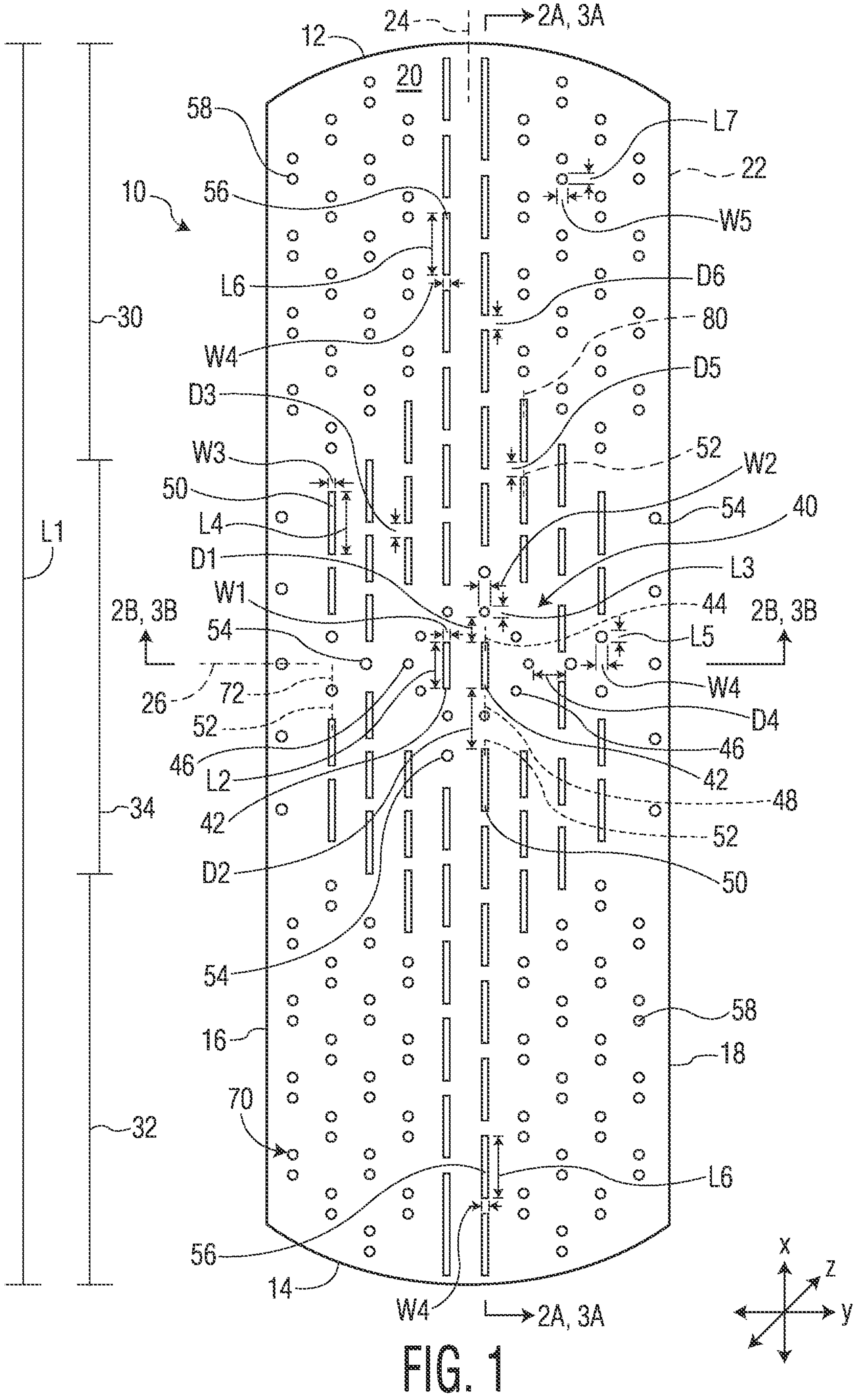
FIG. 1 is a top down view of an embodiment of an absorbent body.

The present disclosure is generally directed towards an absorbent body for use in an absorbent article which can have an improved body exudate distribution capability. An absorbent body can have a longitudinal direction and a transverse direction. The absorbent body can have an anterior region, a posterior region, and a crotch region located between the anterior region and the posterior region. An exudate capture zone can be located within the crotch region of the absorbent body. The exudate capture zone can have a primary compressed element which is parallel with the longitudinal direction axis and which has a longitudinal direction length greater than a transverse direction width. The primary compressed element within the exudate capture zone can be encircled by a plurality of primary compressed points. Each of the encircled primary compressed element and the encircling primary compressed points can provide an initial pathway for body exudates to travel from the upper surface of the absorbent body in the exudate capture zone and into other regions of the absorbent body in both the longitudinal direction and transverse direction of the absorbent body. Providing pathways for the body exudates to travel can increase the body exudate distribution capability of the absorbent body and decrease the feeling of wetness to the wearer of the absorbent article.

Definitions

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber.

Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD)

which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter.

Thereafter, the meltblown fibers are carried by the high velocity gas stream and are deposited on a collecting surface to form a web of randomly disbursed meltblown fibers. Such a process is disclosed, for example, in U.S. Pat. No. 3,849, 241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Body:

The present disclosure is generally directed towards an absorbent body for use in an absorbent article which can have an improved body exudate distribution capability. An absorbent body can have a longitudinal direction and a transverse direction. The absorbent body can have an anterior region, a posterior region, and a crotch region located between the anterior region and the posterior region. An exudate capture zone can be located within the crotch region of the absorbent body. The exudate capture zone can have a primary compressed element which has a longitudinal direction length greater than a transverse direction width and which has a longitudinal direction axis that is parallel with the longitudinal direction axis of the absorbent body. The primary compressed element within the exudate capture zone can be encircled by a plurality of primary compressed points. Each of the encircled primary compressed element and the encircling primary compressed points can provide an initial pathway for body exudates to travel from the body facing surface of the absorbent body and into other regions of the absorbent body in both the longitudinal direction and transverse direction of the absorbent body. Providing pathways for the body exudates to travel can increase the body exudate distribution capability of the absorbent body and decrease the feeling of wetness to the wearer of the absorbent article. As will be described herein, incorporating compressed elements and compressed points into any of the anterior region, posterior region, or crotch region of the absorbent body is accomplished via compressing the absorbent material of the absorbent body itself with embossing pins prior to including the absorbent body into an absorbent article. Therefore, the compressed elements and compressed points define void areas which are not filled with material of the absorbent body or from any other layer of an absorbent article, such as, for example, the material forming a surge layer or a topsheet layer. Maintaining the void areas of the compressed elements and compressed points free of material from another layer will further enhance the ability of the absorbent body to distribute body exudate. Compressing the absorbent material of the absorbent body can alter the structure of the absorbent body. Prior to compressing the absorbent material to incorporate compressed elements and compressed points, the absorbent material of the absorbent body can have a uniform density.

Compressing the absorbent material will result in portions of the absorbent material of the absorbent body having a higher density (e.g., in the locations of the compressed elements and compressed points) as compared to portions of the absorbent material of the absorbent body having a low density (e.g., in the remaining uncompressed portions of the absorbent material of the absorbent body). While body exudates can enter the absorbent body in the uncompressed portions due to the overall void volume and low density of the absorbent body in the uncompressed portions, the body exudates can more rapidly enter the void areas defined by the compressed elements and compressed points. The void areas, particularly at the base of the void areas defining the base of the compressed elements and compressed points, however, defines portions of the absorbent body which have low void volume and high density. Thus, the body exudates will not rapidly transfer into the actual absorbent material of the absorbent body at the base of the void areas. Rather, in these void areas, the body exudates will travel, unimpeded by absorbent material, quickly throughout the dimension of the void areas until reaching the higher void volume, lower density areas of the uncompressed portions of the absorbent material of the absorbent body. The absorbent material present in the uncompressed portions of the absorbent body can, via capillary action, pull the body exudates from the void areas and continue to transfer the body exudates throughout the absorbent body including into additional void areas of additional compressed elements and compressed points wherein the speed of the movement of the body exudates can increase again. Providing an absorbent body with a pattern of compressed elements and compressed points can result in an absorbent body that has an enhancing capability of distributing body exudates through the absorbent body in both the longitudinal direction and the transverse direction.

Figure 2A:
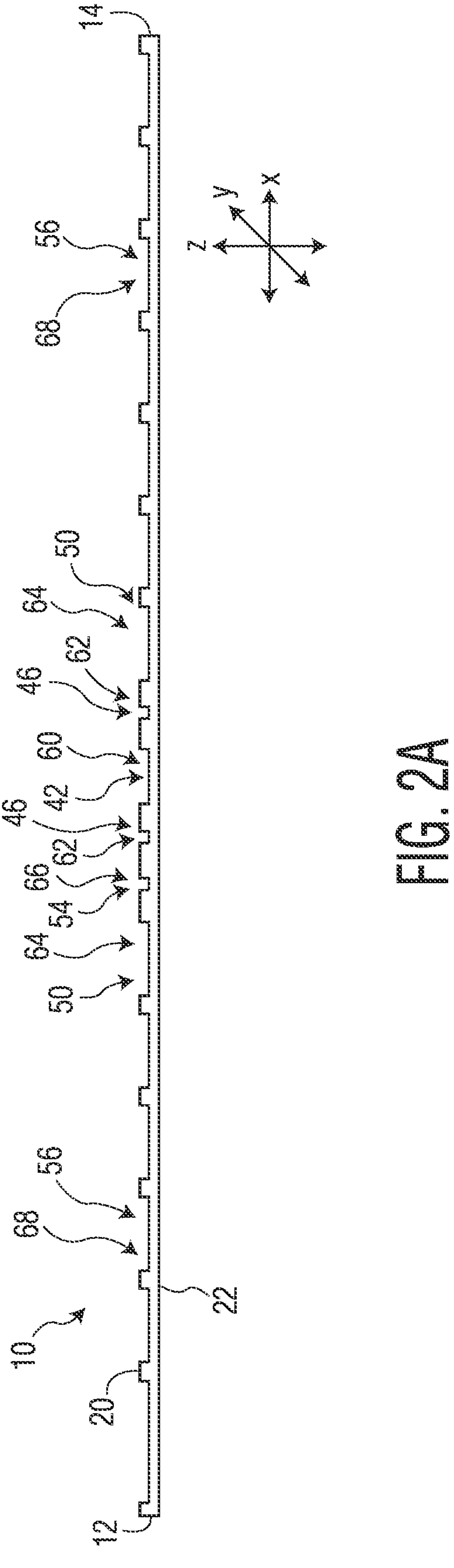
FIG. 2A is a cross-sectional view of an embodiment of the absorbent body of FIG. 1 taken along line 2A-2A.
Figure 2B:
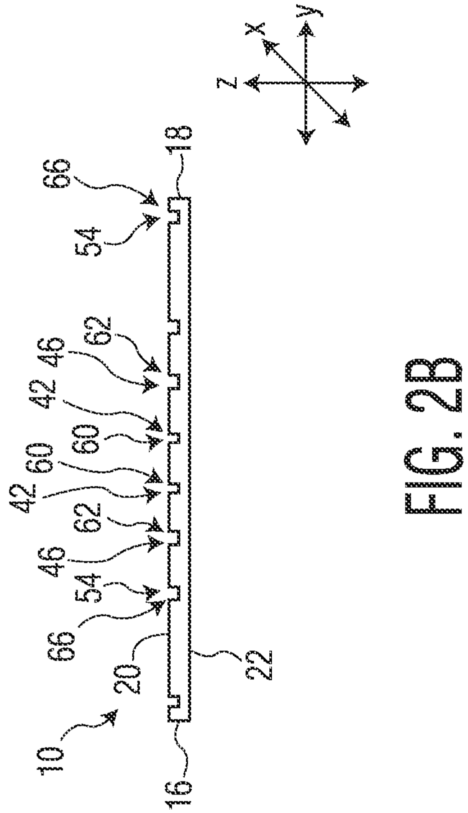
FIG. 2B is a cross-sectional view of an embodiment of the absorbent body of FIG. 1 taken along line 2B-2B.

Referring to FIGS. 1, 2A, and 2B, FIG. 1 provides an exemplary illustration of a top down view of an absorbent body 10, FIG. 2A provides an exemplary illustration of an embodiment of a cross-section of the absorbent body 10 of FIG. 1 taken along line 2A-2A, and FIG. 2B provides an exemplary illustration of an embodiment of a cross-section of the absorbent body 10 of FIG. 1 taken along line 2B-2B. The absorbent body 10 can have a longitudinal direction (X), a transverse direction (Y), and a depth direction (Z). The absorbent body 10 can have a first transverse direction end edge 12, a second transverse direction end edge 14 opposite the first transverse direction end edge 12, and a pair of opposing longitudinal direction side edges, 16 and 18, connecting the first and second transverse direction end edges, 12 and 14. The absorbent body 10 can have a body facing surface 20 which can be the uppermost surface of the absorbent body 10. The absorbent body 10 can have a garment facing surface 22 which can be the bottommost surface of the absorbent body 10. The absorbent body 10 can have a longitudinal direction axis 24 and a transverse direction axis 26.

The absorbent body 10 can generally be any single layer structure or combination of layer components, which can demonstrate some level of compressibility, conformability, be non-irritating to a wearer's skin, and capable of absorbing and retaining liquids and other body exudates. In various embodiments, the absorbent body 10 can be formed from absorbent material which can include absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In various embodiments, the absorbent web material can include a matrix of cellulosic fluff. In various embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent body 10 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent body 10 in any amount as desired.

Regardless of the combination of absorbent materials used in the absorbent body 10, the absorbent materials can be formed into a web structure by employing various conventional methods and techniques. For example, the absorbent web structure can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art. Various woven fabrics and nonwoven webs can be used to construct the absorbent body 10. For example, the absorbent body 10 can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The absorbent body 10 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The bonded carded web can have a basis weight of less than about 100 gsm, and in some embodiments, from about 10 gsm to about 40 gsm.

The shape of the absorbent body 10 can vary as desired and can comprise any one of various shapes including, but not limited to, triangular, rectangular, dog-bone and elliptical shapes. In various embodiments, the absorbent body 10 can have a shape that generally corresponds with the overall shape of the absorbent article 100 within which the absorbent body 10 is used. The dimensions of the absorbent body 10 can be substantially similar to those of the absorbent article 100, however, it will be appreciated that the dimensions of the absorbent body 10 while similar, will often be less than those of the overall absorbent article 100, in order to be adequately contained therein.

By way of example, suitable materials and/or structures for the absorbent body 10 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

The absorbent body 10 can have an anterior region 30, a posterior region 32, and a crotch region 34 located between the anterior region 30 and the posterior region 32. In general, the anterior region 30 is adapted to be positioned towards the front of the wearer of the absorbent article 100 within which the absorbent body 10 is contained, the posterior region 32 is adapted to be positioned towards the back of the wearer of the absorbent article 100, and the crotch region 34 is adapted to be worn proximate to the wearer's crotch. The absorbent body 10 has a total absorbent body length L1, as measured as the distance between the first transverse direction end edge 12 and the second transverse direction end edge 14. In various embodiments, for example, the total absorbent body length L1 can be divided into thirds and the anterior region 30 of the absorbent body can be defined as the first third of the total absorbent body length L1 as measured from the first transverse direction end edge 12, the crotch region 34 can be defined as the second third of the total absorbent body length L1, and the posterior region 32 can be defined as the final third of the total absorbent body length L1 and includes the second transverse direction end edge 14. It is to be understood that the lengths of each of the anterior region 30, the crotch region 34, and the posterior region 32 can vary as deemed suitable for usage of the absorbent body 10 in an absorbent article 100. In various embodiments, for example, either or both of the anterior region 30 and/or the crotch region 34 can have a longitudinal direction length of less than a third of the total absorbent body length L1 while the posterior region 32 can have a longitudinal direction length of greater than a third of the total absorbent body length L1.

An exudate capture zone 40 is located within the crotch region 34 of the absorbent body 10. The exudate capture zone 40 can be the portion of the absorbent body 10 within the absorbent article 100 that initially receives body exudates from the wearer of the absorbent article 100 and can enhance the ability of the absorbent body 10 to transfer body exudates in the depth direction (Z) from the body facing surface 20 of the absorbent body 10 into and throughout the absorbent body 10 in the longitudinal direction (X) as well as the transverse direction (Y). In various embodiments, the exudate capture zone 40 can be located at the intersection of the longitudinal direction axis 24 and the transverse direction axis 26 of the absorbent body 10 and can be symmetrical about each of the longitudinal direction axis 24 and the transverse direction axis 26, such as, for example, illustrated in FIGS. 1 and 4. In various embodiments, the exudate capture zone 40 can be positioned in a symmetrical configuration about the longitudinal direction axis 24 and positioned between the transverse direction axis 26 and the first transverse direction end edge 12 of the absorbent body 10.

In various embodiments, the exudate capture zone 40 can be positioned in a symmetrical configuration about the longitudinal direction axis 24 and positioned such that at least portion of the exudate capture zone 40 crosses over the transverse direction axis 26 of the absorbent body 10.

The exudate capture zone 40 can have at least one primary compressed element 42. In various embodiments, the exudate capture zone 40 can have at least 1, 2, 3, or 4 primary compressed elements 42. Referring to the exemplary embodiments illustrated in FIGS. 1 and 4, the exudate capture zone 40 of the absorbent body 10 is illustrated as having 2 primary compressed elements 42.

Each primary compressed element 42 within the exudate capture zone 40 is formed by compressing the material forming the absorbent body 10 and, therefore, each primary compressed element 42 extends into the absorbent material forming the absorbent body 10. Compression of the absorbent material of the absorbent body 10 can occur by utilizing embossing pins wherein the embossing pin has the shape desired for the primary compressed element 42. For example, an embossing pin can have a rectangular shape which can produce a primary compressed element 42 having a rectangular shape. A primary compressed element 42 can have a size dimension deemed suitable for providing the desired exudate distribution capability. In various embodiments, a primary compressed element 42 within the exudate capture zone 40 can have a length L2 in the longitudinal direction (X) from 7, 8, or 9 mm to 18, 19, or 20 mm. A primary compressed element 42 within the exudate capture zone 40 can have a length L2 in the longitudinal direction (X) which is greater than its width W1 in the transverse direction (Y). A primary compressed element 42 within the exudate capture zone 40 can have a width W1 in the transverse direction (Y) from 1, 1.5, or 2 mm to 3, 3.5, or 4 mm. By utilizing an embossing pin to compress the absorbent material thereby incorporating the primary compressed element 42 into the absorbent body 10, a void area 60 can be created within the absorbent body 10 without the actual removal of any of the absorbent material from the absorbent body 10. The void area 60 of the primary compressed element 42 will have a size dimension corresponding to the embossing pin dimensions and will have a longitudinal direction (X) dimension that is greater than the transverse direction (Y) dimension. Due to the lack of absorbent material in the void area 60, the body exudates can enter the void area 60 of the primary compressed element 42 more rapidly than in the uncompressed areas of the absorbent body 10 and can then travel unimpeded along the void area 60 in the longitudinal direction (X) of the absorbent body 10. The presence of a primary compressed element 42 in the exudate capture zone 40 can provide the absorbent body 10 with a pathway for the body exudates to travel from the body facing surface 20 of the absorbent body 10 and into the absorbent material of the absorbent body 10. As the primary compressed element 42 has a length L2 in the longitudinal direction (X) larger than its width W1 in the transverse direction (Y), the body exudates can travel unimpeded a further distance in the longitudinal direction (X) of the absorbent body 10. Providing pathways for the body exudates to travel can increase the exudate distribution capability of the absorbent body 10 and decrease the feeling of wetness to the wearer of the absorbent article 100. A primary compressed element 42 in the exudate capture zone 40 has a longitudinal direction axis 44 which is parallel to the longitudinal direction axis 24 of the absorbent body 10. In various embodiments, the longitudinal direction axis 44 of a primary compressed element 42 within the exudate capture zone 40 is in an overlapping configuration with the longitudinal direction axis 24 of the absorbent body 10. In various embodiments, the longitudinal direction axis 44 of a primary compressed element 42 within the exudate capture zone 40 is offset, in the transverse direction (Y), from the longitudinal direction axis 24 of the absorbent body 10.

The primary compressed element(s) 42 within the exudate capture zone 40 is encircled by a plurality of primary compressed points 46. In various embodiments, at least 6, 7, 8, 9, 10, 11, or 12 primary compressed points 46 can encircle the primary compressed element(s) 42 within the exudate capture zone 40. In the exemplary embodiments illustrated in FIGS. 1 and 4, the absorbent body 10 has 10 primary compressed points 46 encircling the two primary compressed elements 42 in the exudate capture zone 40. Each primary compressed point 46 within the exudate capture zone 40 is formed by compressing the material forming the absorbent body 10 and, therefore, each primary compressed point 46 extends into the absorbent material forming the absorbent body 10. Compression of the absorbent material of the absorbent body 10 can occur by utilizing embossing pins wherein each embossing pin has the shape desired for each primary compressed point 46. For example, an embossing pin can have a circular shape which can produce a primary compressed point 46 having a circular shape. Each primary compressed point 46 can have a size dimension deemed suitable for providing the desired exudate distribution capability. In various embodiments, each of the primary compressed points 46 within the exudate capture zone 40 can have a length L3 in the longitudinal direction (X) from 1, 1.5, or 2 mm to 3, 3.5, or 4 mm. Each of the primary compressed points 46 within the exudate capture zone 40 can have a width W2 in the transverse direction (Y) from 1, 1.5, or 2 mm to 3, 3.5, or 4 mm. By utilizing an embossing pin to compress the absorbent material thereby incorporating the primary compressed point 46 into the absorbent body 10, a void area 62 can be created within the absorbent body 10 without the actual removal of any of the absorbent material from the absorbent body 10. Due to the lack of absorbent material in the void area 62, the body exudates can enter the void area 62 of the primary compressed point 46 more quickly than the uncompressed areas of the absorbent body 10 which can, therefore, improve the exudate distribution capability of the absorbent body 10. The void area 62 of the primary compressed points 46 provides an initial well into which the body exudates can collect. The body exudates can then disperse from the void area 62 of each of the primary compressed points 46 in all directions surrounding the primary compressed points 46 and into the absorbent material surrounding the void area 62 via capillary action of the absorbent material pulling the body exudates, thus, enabling improved fluid flow of the body exudates in the longitudinal direction (X) and the transverse direction (Y). The presence of the primary compressed points 46 in the exudate capture zone 40 can provide the absorbent body 10 with a pathway for the body exudates to travel from the body facing surface 20 of the absorbent body 10 and into the absorbent material of the absorbent body 10. Providing pathways for the body exudates to travel can increase the exudate distribution capability of the absorbent body 10 and decrease the feeling of wetness to the wearer of the absorbent article 100.

Each of the primary compressed points 46 in the exudate capture zone 40 have a longitudinal direction axis 48 which is parallel to the longitudinal direction axis 24 of the absorbent body 10. In various embodiments, the longitudinal direction axis 48 of a primary compressed point 46 within the exudate capture zone 40 is in an overlapping configuration with the longitudinal direction axis 24 of the absorbent body 10. In various embodiments, the longitudinal direction axis 48 of a primary compressed point 46 within the exudate capture zone 40 is offset, in the transverse direction (Y), from the longitudinal direction axis 24 of the absorbent body 10. In various embodiments, the longitudinal direction axis 48 of a primary compressed point 46 is aligned, in the longitudinal direction (X), with the longitudinal direction axis 44 of a primary compressed element 42 in the exudate capture zone 40. In embodiments wherein a primary compressed point 46 has a longitudinal direction axis 48 that is aligned with the longitudinal direction axis 44 of a primary compressed element 42 in the exudate capture zone 40 a distance D1, in the longitudinal direction (X) of the absorbent body 10, separating the aligned primary compressed element 42 and the aligned primary compressed point 46 is from 2, 3, or 4 mm to 7, 8, 9, or 10 mm.

Within the crotch region 34 of the absorbent body 10, in addition to the exudate capture zone 40, the absorbent body 10 can have a plurality of secondary compressed elements 50 and a plurality of secondary compressed points 54. The secondary compressed elements 50 and the secondary compressed points 54 are not encircled by the primary compressed points 46 which encircle the primary compressed element(s) 42.

Each secondary compressed element 50 within the crotch region 34 is formed by compressing the material forming the absorbent body 10 and, therefore, each secondary compressed element 50 extends into the absorbent material forming the absorbent body 10. Compression of the absorbent material of the absorbent body 10 can occur by utilizing embossing pins wherein the embossing pin has the shape desired for the secondary compressed element 50. For example, an embossing pin can have a rectangular shape which can produce a secondary compressed element 50 having a rectangular shape. A secondary compressed element 50 can have a size dimension deemed suitable for providing the desired exudate distribution capability. In various embodiments, a secondary compressed element 50 within the crotch region can have a length L4 in the longitudinal direction (X) from 7, 8, or 9 mm to 18, 19, or 20 mm. A secondary compressed element 50 within the crotch region 34 can have a length L4 in the longitudinal direction (X) which is greater than its width W3 in the transverse direction (Y). A secondary compressed element 50 within the crotch region 34 can have a width W3 in the transverse direction (Y) from 1, 1.5, or 2 mm to 3, 3.5, or 4 mm. By utilizing an embossing pin to compress the absorbent material thereby incorporating the secondary compressed element 50 into the absorbent body 10, a void area 64 can be created within the absorbent body 10 without the actual removal of any of the absorbent material from the absorbent body 10. The void area 64 of the secondary compressed element 50 will have a size dimension corresponding to the embossing pin dimension and will have a longitudinal direction (X) dimension that is greater than the transverse direction (Y) dimension. Due to the lack of absorbent material in the void area 64, the body exudates can enter the void area 64 of the secondary compressed element 50 more rapidly than had the absorbent material been uncompressed and can then travel unimpeded along the void area 64 in the longitudinal direction (X) of the absorbent body 10. The presence of a secondary compressed element 50 in the crotch region 34 can provide the absorbent body 10 with a pathway for the body exudates to travel in the longitudinal direction (X) through the absorbent body 10. As the secondary compressed element 50 has a length L4 in the longitudinal direction (X) larger than its width W3 in the transverse direction (Y), the body exudates can travel unimpeded a further distance in the longitudinal direction (X) of the absorbent body 10. Providing pathways for the body exudates to travel can increase the exudate distribution capability of the absorbent body 10 and decrease the feeling of wetness to the wearer of the absorbent article 100.

A secondary compressed element 50 in the crotch region 34 has a longitudinal direction axis 52 which is parallel to the longitudinal direction axis 24 of the absorbent body 10. In various embodiments, the longitudinal direction axis 52 of a secondary compressed element 50 within the crotch region 34 is in an overlapping configuration with the longitudinal direction axis 24 of the absorbent body 10. In various embodiments, the longitudinal direction axis 52 of a secondary compressed element 50 within the crotch region 34 is offset, in the transverse direction (Y), from the longitudinal direction axis 24 of the absorbent body 10. In various embodiments, at least one secondary compressed element 50 is arranged such that its longitudinal direction axis 52 is aligned, in the longitudinal direction (X) of the absorbent body 10, with the longitudinal direction axis 44 of a primary compressed element 42 of the exudate capture zone 40. In embodiments wherein a secondary compressed element 50 has a longitudinal direction axis 52 that is aligned with the longitudinal direction axis 44 of a primary compressed element 42 in the exudate capture zone 40 a distance D2, in the longitudinal direction (X) of the absorbent body 10, separating the aligned primary compressed element 42 and the aligned secondary compressed element 50 is less than 10 mm. In embodiments wherein a secondary compressed element 50 has a longitudinal direction axis 52 that is aligned with the longitudinal direction axis 44 of a primary compressed element 42 in the exudate capture zone 40 a distance D2, in the longitudinal direction (X) of the absorbent body 10, separating the aligned primary compressed element 42 and the aligned secondary compressed element 50 is from 2, 3, or 4 mm to 7, 8, 9, or 10 mm. The distance D2 between an aligned primary compressed element 42 and an aligned secondary compressed element 50 should be less than 10 mm in order to facilitate the exudate distribution capability of the absorbent body 10 in the longitudinal direction (X) of the absorbent body 10. The body exudate can move more rapidly in the longitudinal direction (X) of the absorbent body 10 initially through the void area 60 of the primary compressed element 42 and then, secondarily, through the void area 64 of the secondary compressed element 50. The uncompressed absorbent material present between the aligned primary compressed element 42 and the aligned secondary compressed element 50 can assist in pulling the fluid of the body exudate from the primary compressed element 42 to the secondary compressed element 50 via capillary action such that the body exudate can continue to flow throughout the absorbent body 10 and particularly in the longitudinal direction (X) of the absorbent body 10. In embodiments wherein D2 is greater than 10 mm, the fluid flow of the body exudates may be too slow due to the presence of the higher amount of absorbent material obstructing its path and can, therefore, result in less movement of the body exudates throughout the absorbent body 10, particularly in the longitudinal direction (X) of the absorbent body 10. In various embodiments, at least one secondary compressed element 50 is arranged such that its longitudinal direction axis 52 is aligned, in the longitudinal direction (X) of the absorbent body 10, with the longitudinal direction axis 52 of a neighboring secondary compressed element 50. In embodiments wherein a secondary compressed element 50 has a longitudinal direction axis 52 that is aligned with the longitudinal direction axis 52 of a neighboring secondary compressed element 50 a distance D3, in the longitudinal direction (X) of the absorbent body 10, separating the aligned neighboring secondary compressed elements 50 is less than 10 mm. In embodiments wherein a secondary compressed element 50 has a longitudinal direction axis 52 that is aligned with the longitudinal direction axis 52 of a neighboring secondary compressed element 50 a distance D3, in the longitudinal direction (X) of the absorbent body 10, separating the aligned neighboring secondary compressed elements 50 is from 2, 3, or 4 mm to 7, 8, 9, or 10 mm. The distance D3 between aligned neighboring secondary compressed elements 50 should be less than 10 mm to facilitate the exudate distribution capability of the absorbent body 10 in the longitudinal direction (X) of the absorbent body 10. The uncompressed absorbent material present between the aligned neighboring secondary compressed elements 50 can assist in pulling the fluid of the body exudate from one secondary compressed element 50 to the neighboring secondary compressed element 50 via capillary action such that the body exudate can continue to flow throughout the absorbent body 10 and particularly in the longitudinal direction (X) of the absorbent body 10. In embodiments wherein D3 is greater than 10 mm, the fluid flow of the body exudates may be too slow due to the presence of the higher amount of absorbent material obstructing its path and can, therefore, result in less movement of the body exudates throughout the absorbent body 10, particularly in the longitudinal direction (X) of the absorbent body 10.

The crotch region 34 can have a plurality of secondary compressed points 54. The plurality of secondary compressed points 54 can be spaced apart from the exudate capture zone 40 in at least the transverse direction (Y) of the absorbent body 10. Each secondary compressed point 54 within the crotch region 34 is formed by compressing the material forming the absorbent body 10 and, therefore, each secondary compressed point 54 extends into the absorbent material forming the absorbent body 10. Compression of the absorbent material of the absorbent body 10 can occur by utilizing embossing pins wherein each embossing pin has the shape desired for each secondary compressed point 54.

For example, an embossing pin can have a circular shape which can produce a secondary compressed point 54 having a circular shape. Each secondary compressed point 54 can have a size dimension deemed suitable for providing the desired exudate distribution capability. In various embodiments, each of the secondary compressed points 54 within the crotch region 34 can have a length L5 in the longitudinal direction (X) from 1, 1.5, or 2 mm to 3, 3.5, or 4 mm. Each of the secondary compressed points 54 within the crotch region 34 can have a width W4 in the transverse direction (Y) from 1, 1.5, or 2 mm to 3, 3.5, or 4 mm. By utilizing an embossing pin to compress the absorbent material thereby incorporating the secondary compressed point 54 into the absorbent body 10, a void area 66 can be created within the absorbent body 10 without the actual removal of any of the absorbent material from the absorbent body 10. The body exudates can enter the void area 66 of the secondary compressed point 54 more quickly than the uncompressed areas of the absorbent body 10 which can, therefore, improve the exudate distribution capability of the absorbent body 10. The void area 66 of the secondary compressed points 54 provides an initial well into which the body exudates can collect. The body exudates can then disperse in all directions from the void area 66 of each of the secondary compressed points 54 and into the absorbent material surrounding the void area 66 of the secondary compressed points 54 via capillary action of the absorbent material pulling the body exudates, thus, enabling improved fluid flow of the body exudates in the longitudinal direction (X) and the transverse direction (Y). The distance D4 between either a primary compressed point 46 and a secondary compressed point 54 or between two neighboring secondary compressed points 54 can be from 2 mm to 4 mm. The distance D4 between two neighboring compressed points in the crotch region 34 is close enough to enable capillary action movement flow of the body exudates through the absorbent material between the neighboring compressed points and void areas. The secondary compressed points 54 in the crotch region 34 can enable distribution of body exudates in both the transverse direction (Y) and the longitudinal direction (X) of the absorbent body 10. The secondary compressed points 54 in the crotch region 34 can enable distribution of body exudates from the secondary compressed points 54 and to secondary compressed elements 50 which are located in the crotch region 34 but spaced apart from, in the transvers direction (Y) and/or the longitudinal direction (X), the exudate capture zone 40. The presence of the secondary compressed points 54 in the crotch region 34 can provide the absorbent body 10 with a pathway for the body exudates to travel which can increase the exudate distribution capability of the absorbent body 10 and decrease the feeling of wetness to the wearer of the absorbent article 100.

The primary compressed element(s) 42 and primary compressed points 46 of the exudate capture zone 40 work with the secondary compressed elements 50 and the secondary compressed points 54 located within the crotch region 34 to enhance intake and distribution of body exudates throughout the remainder of the absorbent body 10. The exudate capture zone 40 can be the initial location for intake of body exudates from the wearer of the absorbent article 100 within which the absorbent body 10 is placed. The primary compressed element 42 has a greater length L2, in the longitudinal direction (X), than width W1, in the transverse direction (Y). The primary compressed element 42 also has a void area 60 which can accept a rapid accumulation of body exudate as well as facilitate distribution of the body exudate, primarily in the longitudinal direction (X) due to the greater length L2 than width W1 and that the body exudate is unimpeded in its movement through the void area 60. The primary compressed points 46 can further accept rapid accumulation of body exudate into the void areas 62 of the primary compressed points 46. The body exudate which has entered the void areas 62 of the primary compressed points 46 can spread, via capillary action, in the longitudinal direction (X) and the transverse direction (Y) through the absorbent material of the absorbent body 10 and can then encounter a secondary compressed element 50 and/or a secondary compressed point 54. Similar to the primary compressed element 52, the secondary compressed element 50 can have a longer length L4 in the longitudinal direction (X) than a width W3 in the transverse direction (Y). The secondary compressed element 50 can also have a void area 64 which can receive the moving body exudate and further facilitate its distribution in the longitudinal direction (X) as the body exudate can be unimpeded in its movement through the void area 64. The moving body exudate which encounters a secondary compressed point 54 can enter the void area 66 of each secondary compressed point 54 where it can be further distributed, via capillary action in the longitudinal direction (X) and the transverse direction (Y), throughout the absorbent material of the absorbent body 10 surrounding the secondary compressed point 54. The moving body exudates can further encounter any of an additional secondary compressed element 50, an additional secondary compressed point 54, or none of the additional secondary compressed elements 50 or secondary compressed points 54. The location, size dimension, and spacing of each of the primary compressed element 42, primary compressed point 46, secondary compressed element 50, and secondary compressed point 54 can enhance the ability of the absorbent body 10 to collect body exudate and distribute the body exudate throughout the longitudinal direction (X) and the transverse direction (Y).

Each of the anterior region 30 and the posterior region 32 can further enhance the ability of the absorbent body 10 to distribute body exudate throughout the absorbent body 10 in each of the longitudinal direction (X) and the transverse direction (Y). Within each of the anterior region 30 and the posterior region 32, the absorbent body 10 can have a plurality of tertiary compressed elements 56 and a plurality of tertiary compressed points 58.

Each tertiary compressed element 56 within the anterior region 30 and posterior region 32 is formed by compressing the material forming the absorbent body 10 and, therefore, each tertiary compressed element 56 extends into the absorbent material forming the absorbent body 10. Compression of the absorbent material of the absorbent body 10 can occur by utilizing embossing pins wherein the embossing pin has the shape desired for the tertiary compressed element 56. For example, an embossing pin can have a rectangular shape which can produce a tertiary compressed element 56 having a rectangular shape. A tertiary compressed element 56 can have a size dimension deemed suitable for providing the desired exudate distribution capability. In various embodiments, a tertiary compressed element 56 within the anterior region 30 and posterior region 32 can have a length L6 in the longitudinal direction (X) from 7, 8, or 9 mm to 18, 19, or 20 mm. A tertiary compressed element 56 within the anterior region 30 and posterior region 32 can have a length L6 in the longitudinal direction (X) which is greater than its width W4 in the transverse direction (Y). A tertiary compressed element 56 within the anterior region 30 and posterior region 32 can have a width W4 in the transverse direction (Y) from 1, 1.5, or 2 mm to 3, 3.5, or 4 mm. By utilizing an embossing pin to compress the absorbent material thereby incorporating the tertiary compressed element 56 into the absorbent body 10, a void area 68 can be created within the absorbent body 10 without the actual removal of any of the absorbent material from the absorbent body 10. The void area 68 of the tertiary compressed element 56 will have a size dimension corresponding to the embossing pin dimension and will have a longitudinal direction (X) dimension that is greater than the transverse direction (Y) dimension. Due to the lack of absorbent material in the void area 68, the body exudates can enter the void area 68 of the tertiary compressed element 56 more rapidly than had the absorbent material been uncompressed and can then travel unimpeded along the void area 68 in the longitudinal direction (X) of the absorbent body 10. The presence of a tertiary compressed element 56 in the anterior region 30 and posterior region 32 can provide the absorbent body 10 with a pathway for the body exudates to travel in the longitudinal direction (X) through the absorbent body 10. As the tertiary compressed element 56 has a length L6 in the longitudinal direction (X) larger than its width W4 in the transverse direction (Y), the body exudates can travel unimpeded a further distance in the longitudinal direction (X) of the absorbent body 10. Providing pathways for the body exudates to travel can increase the exudate distribution capability of the absorbent body 10 and decrease the feeling of wetness to the wearer of the absorbent article 100.

A tertiary compressed element 56 in the anterior region 30 or posterior region 32 has a longitudinal direction axis 80 which is parallel to the longitudinal direction axis 24 of the absorbent body 10. In various embodiments, the longitudinal direction axis 80 of a tertiary compressed element 56 within the anterior region 30 or posterior region 32 is in an overlapping configuration with the longitudinal direction axis 24 of the absorbent body 10. In various embodiments, the longitudinal direction axis 80 of a tertiary compressed element 56 within the anterior region 30 or posterior region 32 is offset, in the transverse direction (Y), from the longitudinal direction axis 24 of the absorbent body 10. In various embodiments, at least one tertiary compressed element 56 is arranged such that its longitudinal direction axis 80 is aligned, in the longitudinal direction (X) of the absorbent body 10, with the longitudinal direction axis 52 of a secondary compressed element 50 in the crotch region 34. In embodiments wherein a tertiary compressed element 56 has a longitudinal direction axis 80 that is aligned with the longitudinal direction axis 52 of a secondary compressed element 50 in the crotch region 34 a distance D5, in the longitudinal direction (X) of the absorbent body 10, separating the aligned secondary compressed element 50 and the aligned tertiary compressed element 56 is less than 10 mm. In embodiments wherein a tertiary compressed element 56 has a longitudinal direction axis 80 that is aligned with the longitudinal direction axis 52 of a secondary compressed element 50 a distance D5, in the longitudinal direction (X) of the absorbent body 10, separating the aligned secondary compressed element 50 and the aligned tertiary compressed element 56 is from 2, 3, or 4 mm to 7, 8, 9, or 10 mm. The distance D5 between an aligned secondary compressed element 50 and an aligned tertiary compressed element 56 should be less than 10 mm in order to facilitate the exudate distribution capability of the absorbent body 10 in the longitudinal direction (X) of the absorbent body 10. The body exudate can move more rapidly in the longitudinal direction (X) of the absorbent body 10 initially through the void area 64 of the secondary compressed element 50 and then, through the void area 68 of the tertiary compressed element 56. The uncompressed absorbent material present between the aligned secondary compressed element 50 and the aligned tertiary compressed element 56 can assist in pulling the fluid of the body exudate from the secondary compressed element 50 to the tertiary compressed element 56 via capillary action such that the body exudate can continue to flow throughout the absorbent body 10 and particularly in the longitudinal direction (X) of the absorbent body 10. In embodiments wherein D5 is greater than 10 mm, the fluid flow of the body exudates may be too slow due to the presence of the higher amount of absorbent material obstructing its path and can, therefore, result in less movement of the body exudates throughout the absorbent body 10, particularly in the longitudinal direction (X) of the absorbent body 10. In various embodiments, at least one tertiary compressed element 56 is arranged such that its longitudinal direction axis 80 is aligned, in the longitudinal direction (X) of the absorbent body 10, with the longitudinal direction axis 80 of a neighboring tertiary compressed element 56. In embodiments wherein a tertiary compressed element 56 has a longitudinal direction axis 80 that is aligned with the longitudinal direction axis 80 of a neighboring tertiary compressed element 56 a distance D6, in the longitudinal direction (X) of the absorbent body 10, separating the aligned neighboring tertiary compressed elements 56 is less than 10 mm. In embodiments wherein a tertiary compressed element 56 has a longitudinal direction axis 80 that is aligned with the longitudinal direction axis 80 of a neighboring tertiary compressed element 56 a distance D6, in the longitudinal direction (X) of the absorbent body 10, separating the aligned neighboring tertiary compressed elements 56 is from 2, 3, or 4 mm to 7, 8, 9, or 10 mm. The distance D6 between aligned neighboring tertiary compressed elements 56 should be less than 10 mm to facilitate the exudate distribution capability of the absorbent body 10 in the longitudinal direction (X) of the absorbent body 10. The uncompressed absorbent material present between the aligned neighboring tertiary compressed elements 56 can assist in pulling the fluid of the body exudate from one tertiary compressed element 56 to the neighboring tertiary compressed element 56 via capillary action such that the body exudate can continue to flow throughout the absorbent body 10 and particularly in the longitudinal direction (X) of the absorbent body 10. In embodiments wherein D6 is greater than 10 mm, the fluid flow of the body exudates may be too slow due to the presence of the higher amount of absorbent material obstructing its path and can, therefore, result in less movement of the body exudates throughout the absorbent body 10, particularly in the longitudinal direction (X) of the absorbent body 10.

The anterior region 30 and posterior region 32 can have a plurality of tertiary compressed points 58. Each tertiary compressed point 58 within the anterior region 30 and posterior region 32 is formed by compressing the material forming the absorbent body 10 and, therefore, each tertiary compressed point 58 extends into the absorbent material forming the absorbent body 10. Compression of the absorbent material of the absorbent body 10 can occur by utilizing embossing pins wherein each embossing pin has the shape desired for each tertiary compressed point 58. For example, an embossing pin can have a circular shape which can produce a tertiary compressed point 58 having a circular shape. Each tertiary compressed point 58 can have a size dimension deemed suitable for providing the desired exudate distribution capability. In various embodiments, each of the tertiary compressed points 58 within the anterior region 30 and posterior region 32 can have a length L7 in the longitudinal direction (X) from 1, 1.5, or 2 mm to 3, 3.5, or 4 mm. Each of the tertiary compressed points 58 within the anterior region 30 and posterior region 32 can have a width W5 in the transverse direction (Y) from 1, 1.5, or 2 mm to 3, 3.5, or 4 mm. By utilizing an embossing pin to compress the absorbent material thereby incorporating the tertiary compressed point 58 into the absorbent body 10, a void area 70 can be created within the absorbent body 10 without the actual removal of any of the absorbent material from the absorbent body 10. The body exudates can enter the void area 70 of the tertiary compressed point 58 more quickly than the uncompressed areas of the absorbent body 10 which can, therefore, improve the exudate distribution capability of the absorbent body 10. The void area 70 of the tertiary compressed points 58 provides an initial well into which the body exudates can collect. The body exudates can then disperse in all directions from the void area 70 of each of the tertiary compressed points 58 and into the absorbent material surrounding the void area 70 of the tertiary compressed points 58 via capillary action of the absorbent material pulling the body exudates, thus, enabling improved fluid flow of the body exudates in the longitudinal direction (X) and the transverse direction (Y).

Figure 4:
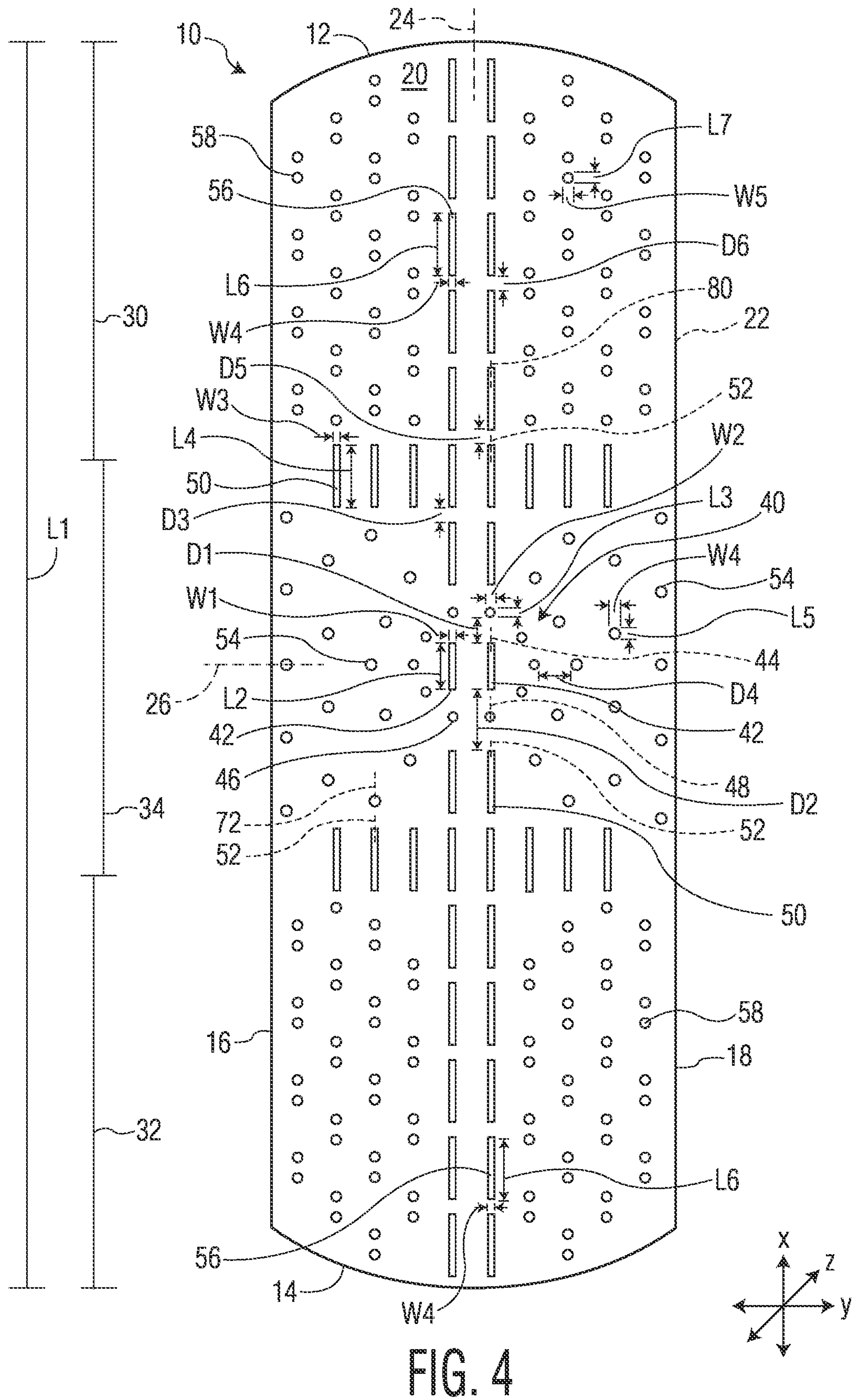
FIG. 4 is a top down view of another embodiment of an absorbent body.

In various embodiments, the absorbent body 10 can have a plurality of pairs of tertiary compressed points 58, such as, for example, illustrated in FIGS. 1 and 4. In various embodiments, a pair of tertiary compressed points 58 can be oriented in the longitudinal direction (X) of the absorbent body 10. In such embodiments, each of the tertiary compressed points 58 of the pair of tertiary compressed points 58 are side-by-side in the longitudinal direction (X) of the absorbent body 10.

In addition to enhancing the ability of the absorbent body 10 to facilitate distribution of body exudates, the tertiary compressed points 58, whether individual or in pairs, can also maintain the integrity and overall structure of the absorbent body absorbent body 10. As the absorbent article 100, within which the absorbent body 10 is placed, is worn it is required to fit and conform to the body of the wearer and maintain its structure through all of the physical movements of the wearer. The incorporation of tertiary compressed points 58, whether individual or in pairs, within the anterior region 30 and posterior region 32 can maintain the overall structure of the absorbent body 10 and help to prevent it from coming apart during the usage of the absorbent article 100.

Figure 3A:
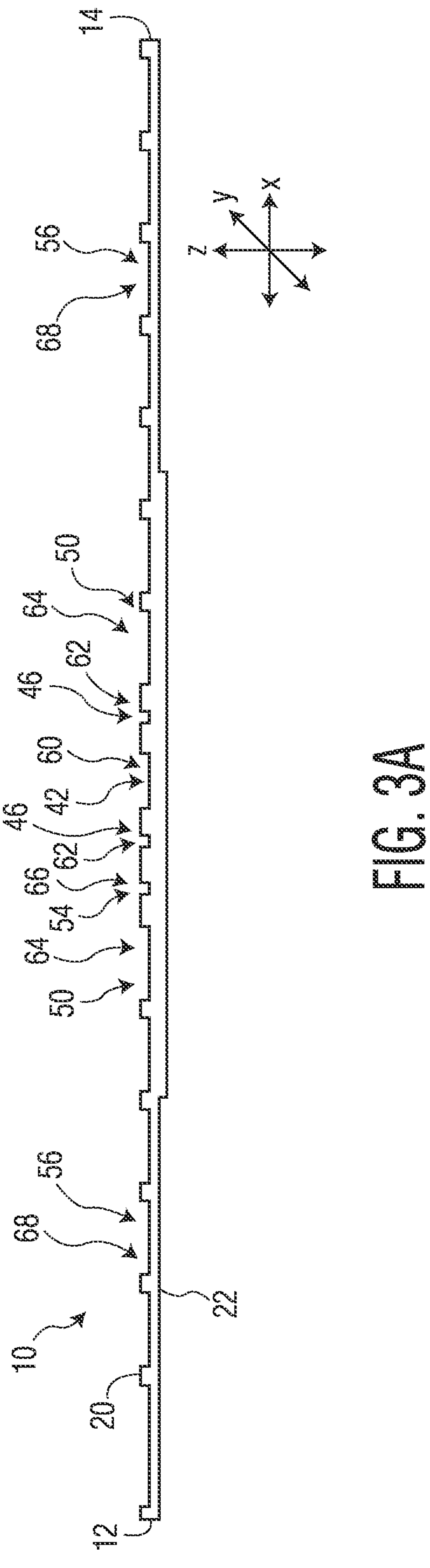
FIG. 3A is a cross-sectional view of another embodiment of the absorbent body of FIG. 1 taken along line 3A-3A.
Figure 3B:
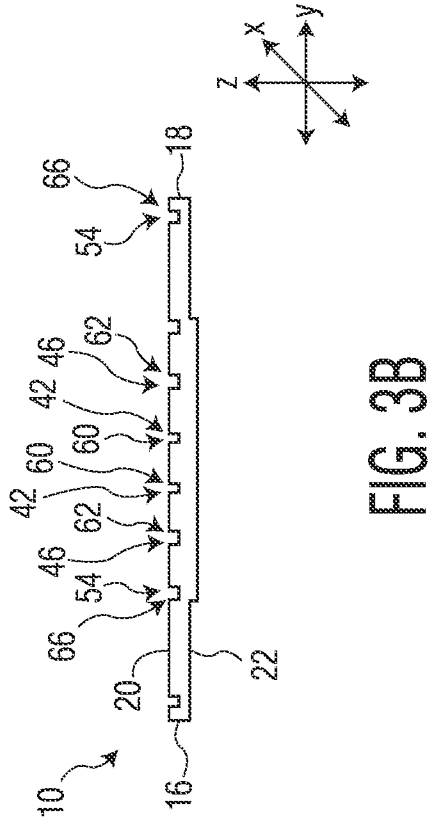
FIG. 3B is a cross-sectional view of another embodiment of the absorbent body of FIG. 1 taken along line 3B-3B.

Utilizing embossing pins to incorporate the compressed elements and the compressed points into the absorbent body 10 results in a compression of the absorbent material forming the absorbent body 10 in the location of the corresponding compressed element and compressed point. In various embodiments, the absorbent body 10 can have a uniform height, measured as the distance between the body facing surface 20 and the garment facing surface 22, prior to the incorporation of the compressed elements and the compressed points. FIGS. 2A and 2B provide an exemplary illustration of an absorbent body 10 having a uniform height between the body facing surface 20 and the garment facing surface 22 in the uncompressed areas of the absorbent body 10. In various embodiments, the absorbent body 10 can have a non-uniform height, measured as the distance between the body facing surface 20 and the garment facing surface 22, prior to the incorporation of the compressed element and the compressed points. FIGS. 3A and 3B provide an exemplary illustration of an absorbent body 10 having a non-uniform height between the body facing surface 20 and the garment facing surface 22 in the uncompressed areas of the absorbent body 10.

In various embodiments, providing an absorbent body 10 with compressed elements and compressed points can improve the ability of the absorbent body 10 to distribute body exudate throughout the absorbent body 10. However, if too many compressed elements and compressed points are incorporated into the absorbent body 10 performance of the absorbent body 10 to absorb and retain body exudates can decrease as a higher area of compressed elements and compressed points can result in an overall increase in the density of the absorbent body 10 and an overall decrease in the void volume of the absorbent body 10. In various embodiments, to maintain a larger void volume of the absorbent body 10 it may be desirable to have a lower area of compressed elements and compressed points with respect to the area of the absorbent body 10 overall. In various embodiments, the proportion of the area of compressed elements and compressed points with respect to the area of the absorbent body 10 can be less than about 15%. In various embodiments, the proportion of the area of compressed elements and compressed points with respect to the area of the absorbent body 10 can be from about 5 or 7% to about 10 or 15%. The lower the area of compressed elements and compressed points with respect to the area of the absorbent body 10 can also provide the absorbent body 10 with flexibility allowing the absorbent body 10, and the overall absorbent article 100, the ability to better conform to the body of the wearer during usage of the absorbent article 100.

Figure 5:
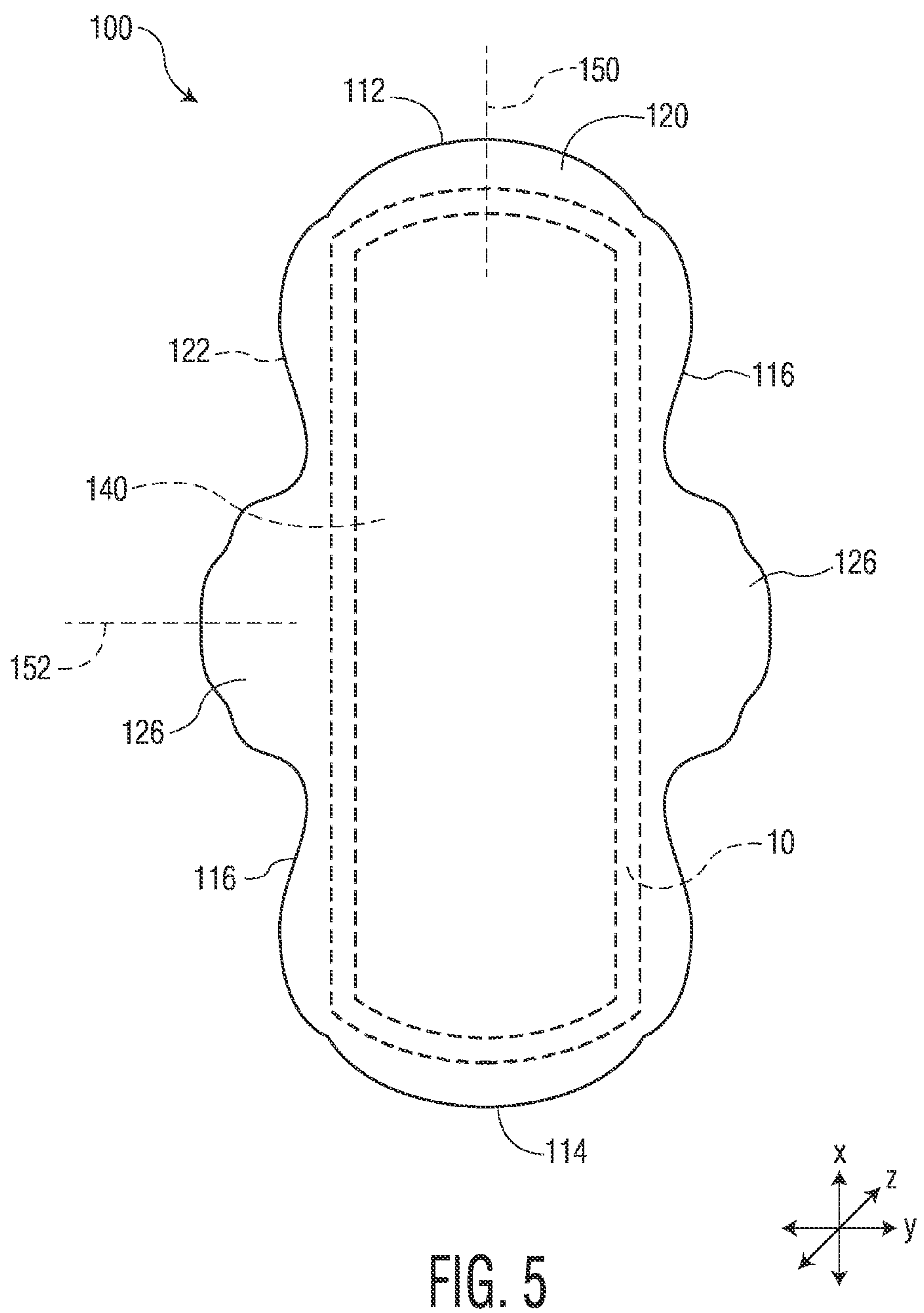
FIG. 5 is a top down view of an embodiment of an absorbent article.
Figure 6:
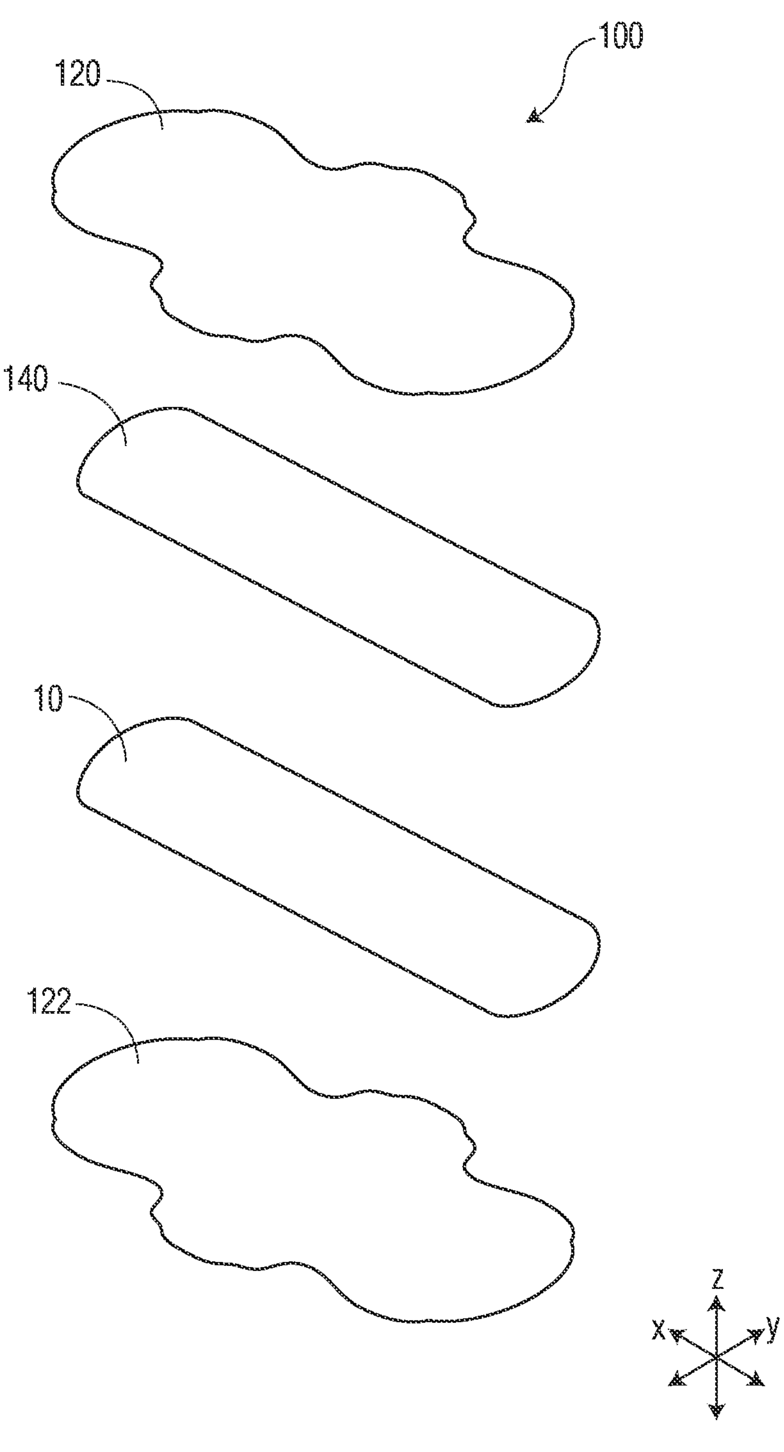
FIG. 6 is an exploded perspective view of the absorbent article of FIG. 5.

Absorbent Article:

The absorbent body 10 of the present disclosure can be incorporated into an absorbent article 100. Referring to FIG. 5, FIG. 5 provides an illustration of a perspective view of an exemplary absorbent article 100. The absorbent article 100 can have a longitudinal direction (X), a transverse direction (Y), and a depth direction (Z). The absorbent article 100 can have a first transverse direction end edge 112, a second transverse direction end edge 114 opposite the first transverse direction end edge 112, and a pair of opposing longitudinal direction side edges 116. In various embodiments, the absorbent article 100 can take on various geometries but will generally have a pair of opposing longitudinal direction side edges 116 and a pair of opposing transverse direction end edges 112 and 114. The absorbent article 100 can have a wearer facing, liquid permeable topsheet layer 120 and a garment facing, liquid impermeable backsheet layer 122. An absorbent body 10 can be positioned between the topsheet layer 120 and the backsheet layer 122. The absorbent article 100 can have a longitudinal axis 150 and a transverse axis 152.

The topsheet layer 120 and the backsheet layer 122 can both extend beyond the outermost peripheral edges of the absorbent body 10 and can be peripherally bonded together, either entirely or partially, using known bonding techniques to form a sealed peripheral region. For example, the topsheet layer 120 and the backsheet layer 122 can be bonded together by adhesive bonding, ultrasonic bonding, or any other suitable bonding method known in the art.

In various embodiments, the absorbent article 100 can have a pair of wings 126 extending outwardly, in the transverse direction T, from the absorbent article 100. The wings 126 can drape over the edges of the wearer's undergarment so that the wings 126 are disposed between the edges of the wearer's undergarment and her thighs. The wings 126 can serve at least two purposes. First, the wings 126 can prevent soiling of the wearer's undergarment by forming a barrier along the edges of the undergarment. Second, the wings 126 can be provided with an attachment aid, such as, for example, a garment attachment adhesive or a hook, to keep the absorbent article 100 securely and properly positioned in the undergarment. The wings 126 can wrap around the crotch region of the wearer's undergarment to aid in securing the absorbent article 100 to the wearer's undergarment when in use. Each wing 126 can fold under the crotch region of the wearer's undergarment and the attachment aid can either form a secure attachment to the opposite wing 126 or directly to the surface of the wearer's undergarment. In various embodiments, the wings 126 can be an extension of materials forming the topsheet layer 120 and/or the backsheet layer 122, such that the wings 126 can be of a unitary construction with the absorbent article 100. In various embodiments, the wings 126 can be constructed of materials similar to the topsheet layer 120, the backsheet layer 122 or combinations of these materials. In various embodiments, the wings 126 can be separate elements bonded to the main body of the absorbent article 100. It is to be understood that the wings 126 are optional and, in various embodiments, an absorbent article 100 can be configured without wings 126.

Topsheet Layer:

The topsheet layer 120 defines a wearer facing surface of the absorbent article 100 that may directly contact the body of the wearer and is liquid permeable to receive body exudates. The topsheet layer 120 is desirably provided for comfort and conformability and functions to direct body exudates away from the body of the wearer, through its own structure, and towards the absorbent body 10. The topsheet layer 120 desirably retains little to no liquid in its structure, so that it provides a relatively comfortable and non-irritating surface next to the skin of the wearer of the absorbent article 100.

The topsheet layer 120 can be a single layer of material, or alternatively, can be multiple layers that have been laminated together. The topsheet layer 120 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 120.

In various embodiments, the topsheet layer 120 can be constructed from various nonwoven webs such as meltblown webs, spunbond webs, hydroentangled spunlace webs, or through air bonded carded webs. Examples of suitable topsheet layer 120 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 120 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 120, each of which is hereby incorporated by reference thereto in its entirety. Additional topsheet layer 120 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 120 may contain a plurality of apertures formed therethrough to permit body exudates to pass more readily into the absorbent body 10. The apertures may be randomly or uniformly arranged throughout the topsheet layer 120. The size, shape, diameter, and number of apertures may be varied to suit an absorbent article's 100 particular needs.

In various embodiments, the topsheet layer 120 can have a basis weight ranging from about 5, 10, 15, 20 or 25 gsm to about 50,100,120, 125 or 150 gsm. For example, in an embodiment, a topsheet layer 120 can be constructed from a through air bonded carded web having a basis weight ranging from about 15 gsm to about 100 gsm. In another example, a topsheet layer 120 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 120 can be at least partially hydrophilic. In various embodiments, a portion of the topsheet layer 120 can be hydrophilic and a portion of the topsheet layer 120 can be hydrophobic. In various embodiments, the portions of the topsheet layer 120 which can be hydrophobic can be either an inherently hydrophobic material or can be a material treated with a hydrophobic coating.

Figure 7:
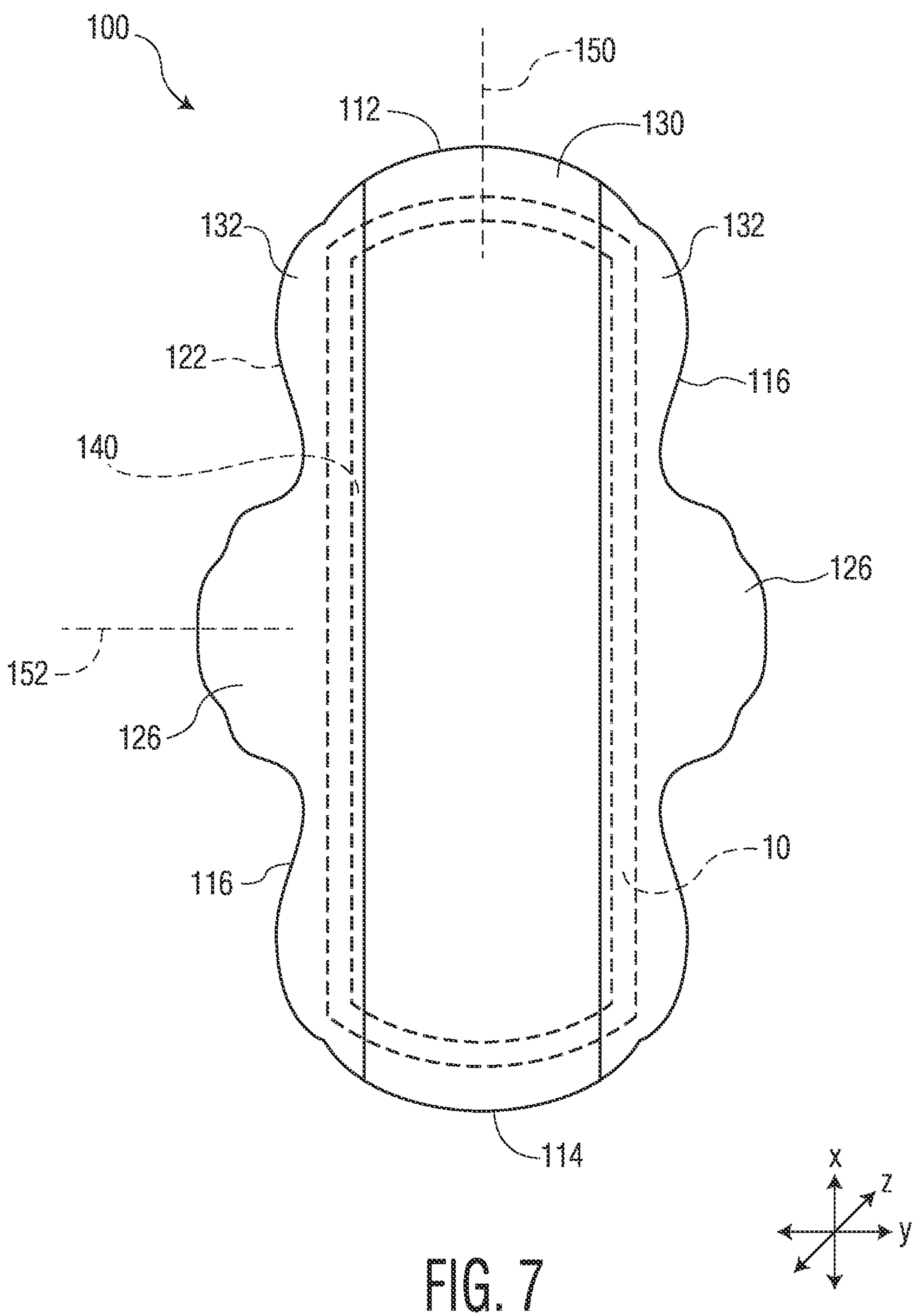
FIG. 7 is a top down view of another embodiment of an absorbent article.
Figure 8:
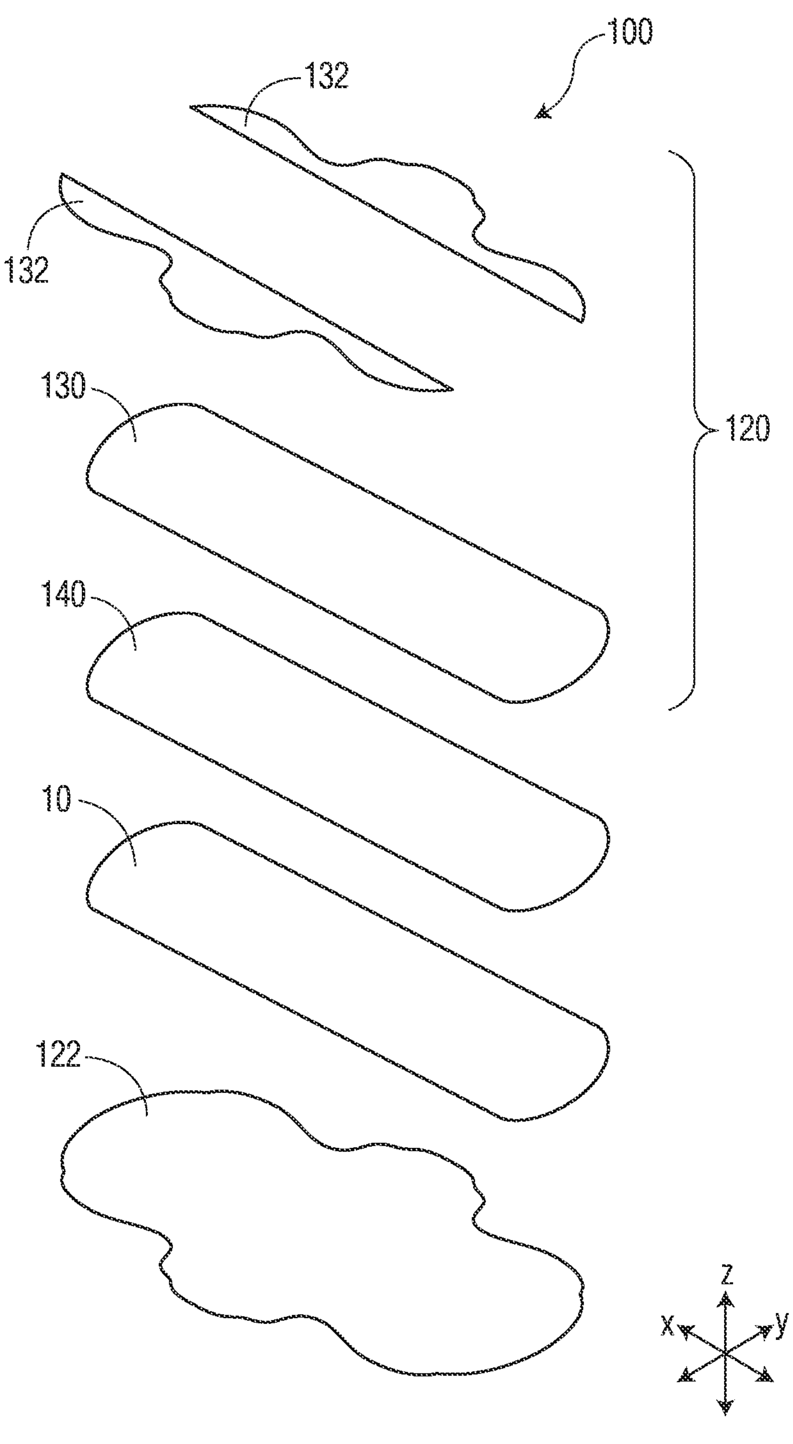
FIG. 8 is an exploded perspective view of the absorbent article of FIG. 7.

In various embodiments, the topsheet layer 120 can be a multicomponent topsheet layer 120 such as by having two or more different nonwoven or film materials, with the different materials placed in separate locations in the transverse direction T of the absorbent article 100. For example, referring to FIGS. 7 and 8, the topsheet layer 120 can be a two layer or multicomponent material having a central portion 130 positioned along and straddling a longitudinal axis 150 of the absorbent article 100, with lateral side portions 132 flanking and bonded to each side edge of the central portion 130. The central portion 130 can be constructed from a first material and the side portions 132 can be constructed from a material which can be the same as or different from the material of the central portion 130. In such embodiments, the central portion 130 may be at least partially hydrophilic and the side portions may be inherently hydrophobic or may be treated with a hydrophobic coating. Examples of constructions of multi-component topsheet layers 120 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion 130 of a topsheet layer 120 can be positioned symmetrically about the absorbent article 100 longitudinal axis 150. Such central longitudinally directed central portion 130 can be a through air bonded carded web ("TABCW") having a basis weight between about 15 and about 100 gsm. Previously described nonwoven, woven, and apertured film topsheet layer materials may also be used as the central portion 130 of a topsheet layer 120. In various embodiments, the central portion 130 can be constructed from a TABCW material having a basis weight from about 20 to about 50 gsm such as is available from Xiamen Yanjan Industry, Beijing, DaYuan Nonwoven Fabrics, and others. Alternatively, apertured films, such as those available from such film suppliers as Texol, Italy and Tredegar, U.S.A. may be utilized. Different nonwoven, woven, or film sheet materials may be utilized as the side portions 132 of the topsheet layer 120. The selection of such topsheet layer 120 materials can vary based upon the overall desired attributes of the topsheet layer 120. For example, it may be desired to have a hydrophilic material in the central portion 130 and hydrophobic-barrier type materials in the side portions 132 to prevent leakage and increase a sense of dryness in the area of the side portions 132. Such side portions 132 can be adhesively, thermally, ultrasonically, or otherwise bonded to the central portion 130 along or adjacent the longitudinally directed side edges of the central portion 130. Traditional absorbent article construction adhesive may be used to bond the side portions 132 to the central portion 130. Either of the central portion 130 and/or the side portions 132 may be treated with surfactants and/or skin-health benefit agents, as are well known in the art.

Such longitudinally directed side portions 132 can be of a single or multi-layered construction. In various embodiments, the side portions 132 can be adhesively or otherwise bonded laminates. In various embodiments, the side portions 132 can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 120 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 100 side edges when viewed from above the topsheet layer 120. The film layer may also serve as a barrier layer to prevent rewet of the topsheet layer 120 as well as to prevent the flow of fluid off the side edges of the absorbent article 100. In various embodiments, the side portions 132 can be laminates such as a spunbond-meltblown-meltblown-spunbond layer ("SMMS") laminate, spunbond-film laminate, or alternatively, other nonwoven laminate combinations.

Surge Layer:

An additional layer in the absorbent article 10 can be a surge layer 140. A surge layer 140 can be constructed of any woven or nonwoven material that is easily penetrated by body exudates. The surge layer 140 can help to absorb, decelerate, and diffuse surges or gushes of liquid that may be rapidly introduced into the absorbent article 100. The surge layer 140 can rapidly accept and temporarily hold the liquid prior to releasing the liquid into, for instance, the absorbent body 10. Various woven fabrics and nonwoven webs can be used to construct the surge layer 140. For example, the surge layer 140 can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layer 140 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layer 140 typically has a basis weight of less than about 100 gsm, and in some embodiments, from about 10 gsm to about 40 gsm.

The surge layer 140 can be incorporated into the absorbent article 10 in any suitable size and shape based upon the need of the particular absorbent article 100 in which the surge layer 140 is being used. In various embodiments, the surge layer 140 can extend across the entire absorbent article 100 in the longitudinal direction and transverse direction, such that the surge layer 140 can have the same dimensions as the topsheet layer 120. In various embodiments, the surge layer 140 can have a smaller overall length in the longitudinal direction and a smaller overall width in the transverse direction than the topsheet layer 120. In various embodiments, the overall length of the surge layer 140 can be from about 30, 40 or 50% to about 98, 99 or 100% of the overall length of the topsheet layer 120. In various embodiments, the overall width of the surge layer 140 can be from about 10, 25 or 50% to about 98, 99 or 100% of the overall width of the topsheet layer 120.

Backsheet Layer:

The backsheet layer 122 is generally liquid impermeable and is the portion of the absorbent article 100 which faces the garment of the wearer. The backsheet layer 122 can permit the passage of air or vapor out of the absorbent article 10 while still blocking the passage of liquids. Any liquid impermeable material may generally be utilized to form the backsheet layer 122. The backsheet layer 122 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 122 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 122 can be a polyethylene film such as that obtainable from Pliant Corporation, Schaumburg, IL, USA. Another example can include calcium carbonate-filled polypropylene film. In still another embodiment, the backsheet layer 122 can be a hydrophobic nonwoven material with water barrier properties such as a nonwoven laminate, an example of which can be a spunbond, meltblown, meltblown, spunbond, four-layered laminate. The backsheet layer 122 can, therefore, be of a single or multiple layer construction, such as of multiple film layers or laminates of film and nonwoven fibrous layers. Suitable backsheet layers 122 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and 6,376,095 to Cheung, et al., each of which are hereby incorporated by reference thereto in its entirety.

Wings:

The wings 126 can be constructed from materials described above with respect to the topsheet layer 120 and the backsheet layer 122. In various embodiments, the wings 126 can comprise an extension of a layer of material within the topsheet layer 120 and/or the backsheet layer 122. By way of example, the wings 126 can be formed by an extension of the topsheet layer 120 and backsheet layer 122 that are then bonded together along peripheral seal 124. Such wings 126 can be integrally formed with the main portion of the absorbent article 100. Alternatively, the wings 126 can be formed independently and separately attached to an intermediate section of the absorbent article 100. Wings 126 that are made independent of the other components of the absorbent article 100 can be bonded to a portion of the topsheet layer 120 and/or backsheet layer 122. Examples of processes for manufacturing absorbent articles 100 and wings 126 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No. 2004/0040650 to Venturino, et al., and international publication WO1997/040804 to Emenaker, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent body comprising:

a longitudinal direction and a transverse direction;

a longitudinal direction axis and a transverse direction axis;

an anterior region, a posterior region, and a crotch region located between the anterior region and the posterior region;

an exudate capture zone located within the crotch region, the exudate capture zone comprising:

a first primary compressed element having a first longitudinal direction axis, a first longitudinal direction length, and a first transverse direction width, wherein the first longitudinal direction length is greater than the first transverse direction width and wherein the first longitudinal direction axis is parallel with the longitudinal direction axis of the absorbent body;

a plurality of primary compressed points encircling the first primary compressed element wherein each of the plurality of primary compressed points has a second longitudinal direction length and a second transverse direction width, wherein the first longitudinal direction length of the first primary compressed element is greater than the second longitudinal direction length and the second transverse direction width of each of the primary compressed points of the plurality of primary compressed points encircling the first primary compressed element; and wherein the first primary compressed element comprises a first void area that is free of material, and each of the plurality of primary compressed points comprises a second void area that is free of material.

2. The absorbent body of claim 1 wherein the first longitudinal direction length of the first primary compressed element is from 7 to 20 mm and the first transverse direction width of the first primary compressed element is from 1 to 4 mm.

3. The absorbent body of claim 1 wherein the second longitudinal direction length of each of the primary compressed points of the plurality of primary compressed points is from 1 to 4 mm and wherein the second transverse direction width of each of the primary compressed points of the plurality of primary compressed points is from 1 to 4 mm.

4. The absorbent body of claim 1 wherein the first longitudinal direction axis of the first primary compressed element is aligned in the longitudinal direction with a second longitudinal direction axis of one of the primary compressed points of the plurality of primary compressed points.

5. The absorbent body of claim 4 wherein the aligned primary compressed element and primary compressed point are separated from each other by a first distance, in the longitudinal direction of the absorbent body, from 2 to 10 mm.

6. The absorbent body of claim 1 further comprising a second primary compressed element parallel with the first primary compressed element and encircled by the plurality of primary compressed points, wherein the second primary compressed element has a second longitudinal direction axis, a second longitudinal direction length, and a second transverse direction width, wherein the second longitudinal direction length is greater than the second transverse direction width and wherein the second longitudinal direction axis is parallel with the longitudinal direction axis of the absorbent body.

7. The absorbent body of claim 6 wherein the second longitudinal direction length of the second primary compressed element is from 7 to 20 mm and the second transverse direction width of the second primary compressed element is from 1 to 4 mm.

8. The absorbent body of claim 1 further comprising a plurality of secondary compressed elements within the crotch region.

9. The absorbent body of claim 8 wherein one of the plurality of secondary compressed elements has a second longitudinal direction axis which is aligned in the longitudinal direction with the first longitudinal direction axis of the first primary compressed element and wherein the first primary compressed element is separated, in the longitudinal direction, from the aligned secondary compressed element by a distance of less than 10 mm.

10. The absorbent body of claim 1 further comprising a plurality of secondary compressed points within the crotch region.

11. The absorbent body of claim 1 further comprising a plurality of tertiary compressed elements in each of the anterior region and posterior region of the absorbent body.

12. The absorbent body of claim 1 further comprising a plurality of tertiary compressed points in each of the anterior region and posterior region of the absorbent body.

13. The absorbent body of claim 1 wherein the proportion of the area of the compressed element and compressed points with respect to the area of the absorbent body is less than 15%.

14. An absorbent article comprising:

a topsheet layer;

a backsheet layer; and the absorbent body of claim 1.

15. The absorbent article of claim 14 further comprising a surge layer positioned between the absorbent body and the topsheet layer.

16. An absorbent body comprising:

a longitudinal axis and a transverse axis perpendicular to the longitudinal axis;

an anterior region, a posterior region, and a crotch region located between the anterior region and the posterior region;

a plurality of compressed elements in the anterior region, the posterior region, and the crotch region, each of the plurality of compressed elements including a void that is a rectangular shape having a length and a width, wherein the length is longer than the width, and the length runs parallel to the longitudinal axis; and a plurality of compressed points in the anterior region, the posterior region, and the crotch region.

17. The absorbent body of claim 16, wherein the plurality of compressed elements comprises primary compressed elements, secondary compressed elements, and tertiary compressed elements;

wherein:

the primary compressed elements are in an exudate capture zone of the crotch region;

the secondary compressed elements are in the crotch region, at least one of the secondary compressed elements being aligned with at least one of the primary compressed elements;

the tertiary compressed elements are in the anterior region and the posterior region, at least one of the tertiary compressed elements being aligned with at least one of the secondary compressed elements.

18. The absorbent body of claim 17, wherein the secondary compressed elements are arranged along eight axes parallel to the longitudinal axis.

19. The absorbent body of claim 16, wherein the plurality of compressed points in the anterior region and the posterior region are arranged along eight axes parallel to the longitudinal axis.

20. An absorbent article comprising the absorbent body of claim 16.

* * * * *